US012758455B2

(12) United States Patent
Johnson

(10) Patent No.: US 12,758,455 B2
(45) Date of Patent: Oct. 13, 2026

(54) KYPHOTIC LIFT FOR MRI IMAGING BED

(71) Applicant: University of Utah Research Foundation, Salt Lake City, UT (US)

(72) Inventor: Brandon Bruce Johnson, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 554 days.

(21) Appl. No.: 17/680,662

(22) Filed: Feb. 25, 2022

(65) Prior Publication Data

US 2022/0280366 A1 Sep. 8, 2022

Related U.S. Application Data

(60) Provisional application No. 63/179,898, filed on Apr. 26, 2021, provisional application No. 63/153,866, filed on Feb. 25, 2021.

(51) Int. Cl.
*A61G 13/06* (2006.01)
*A61B 5/00* (2006.01)
(Continued)

(52) U.S. Cl.
CPC .............. *A61G 13/06* (2013.01); *A61B 5/055* (2013.01); *A61B 5/704* (2013.01); *A61G 13/08* (2013.01); *A61G 13/122* (2013.01)

(58) Field of Classification Search
CPC .................. A61G 7/065; A61G 7/1021; A61G 2200/327; A61G 2200/32; A61G 2200/325; A61G 13/08; A61G 13/06; A61G 13/122; A61G 13/1225; A61G 13/123; A61G 13/1255; A61G 13/121; A61G 13/1215; A61G 13/1205; A61G 13/12;
(Continued)

(56) References Cited

U.S. PATENT DOCUMENTS 4,895,173 A * 1/1990 Brault ...................... A61G 1/01 128/870
4,977,629 A * 12/1990 Jones ..................... A61G 7/001 5/632
(Continued)

FOREIGN PATENT DOCUMENTS

CN 112263239 A 1/2021
EP 3466391 4/2019
(Continued)

OTHER PUBLICATIONS

Written Opinion for International Application Serial No. PCT/US22/17847 dated Jun. 16, 2022, 10 pages, United States.
(Continued)

*Primary Examiner* — Justin C Mikowski
(74) *Attorney, Agent, or Firm* — Workman Nydegger

(57) ABSTRACT

A kyphotic lift can comprise a support base, and a body support secured to the support base. The body support can be movable away from the support base and can be operable to support at least an upper body of the patient during use. The kyphotic lift can also comprise a lift mechanism operable to raise and lower the body support away from and back towards the support base to position and align a head of the patient with a magnetic resonance imaging (MRI) head coil.

29 Claims, 7 Drawing Sheets

(51) Int. Cl.

| | |
|---|---|
| ***A61B 5/055*** | (2006.01) |
| ***A61G 13/08*** | (2006.01) |
| ***A61G 13/12*** | (2006.01) |

(58) Field of Classification Search

CPC .............. A61G 13/1265; A61G 13/126; A61G 13/127; A61G 13/1275; A61G 13/128; A61G 13/0054; A61G 1/04; A61B 5/702; A61B 5/704; A61B 5/70; A61B 5/055; A61B 6/0485; A61B 6/0487; A61B 6/0407

See application file for complete search history.

(56) References Cited

U.S. PATENT DOCUMENTS

| | | | | |
|---|---|---|---|---|
| 5,809,597 | A | 9/1998 | Shaw | |
| 6,267,447 | B1 * | 7/2001 | Hendry | B60P 1/16 298/22 R |
| 6,357,066 | B1 | 3/2002 | Pierce | |
| 6,360,387 | B1 * | 3/2002 | Everhart | A47C 20/027 5/490 |
| 6,725,481 | B1 | 4/2004 | Marshall | |
| 6,882,877 | B2 | 4/2005 | Bonutti | |
| 7,243,387 | B2 | 7/2007 | Schindler | |
| 8,011,045 | B2 | 9/2011 | Skripps | |
| 10,244,994 | B2 | 4/2019 | Davis | |
| 2004/0098803 | A1 * | 5/2004 | Schindler | A61B 5/055 5/601 |
| 2004/0220467 | A1 * | 11/2004 | Bonutti | A61B 6/0421 600/407 |
| 2009/0003532 | A1 * | 1/2009 | Weber | A61B 6/0487 378/209 |
| 2012/0011658 | A1 | 1/2012 | Weedling et al. | |
| 2012/0323113 | A1 * | 12/2012 | Biber | A61B 5/055 600/422 |
| 2013/0062922 | A1 | 3/2013 | Dickson | |
| 2013/0239331 | A1 | 9/2013 | Eaton et al. | |
| 2014/0243716 | A1 * | 8/2014 | Diot | A61G 7/075 601/5 |
| 2015/0157521 | A1 * | 6/2015 | Williams | A61H 23/006 5/81.1 R |
| 2015/0323621 | A1 * | 11/2015 | Noras | A61B 17/3403 600/423 |
| 2016/0151222 | A1 | 6/2016 | Pedro et al. | |
| 2019/0008720 | A1 | 1/2019 | Joshi et al. | |
| 2020/0022613 | A1 * | 1/2020 | Nelson | G01R 33/445 |
| 2020/0094104 | A1 * | 3/2020 | Graham | A61F 5/028 |
| 2021/0161304 | A1 * | 6/2021 | Reinhard | A47C 9/002 |

FOREIGN PATENT DOCUMENTS

| | | | |
|---|---|---|---|
| WO | WO 1998/055070 | A1 | 12/1998 |
| WO | 0057829 | | 10/2000 |

OTHER PUBLICATIONS

Bulbhead; “BulbHead Ramp Must-Have Elevating Rest Relieves Leg, Hip and Knee Pain, Improves Circulation, Reduces Swelling-Inflatable Bed Wedge Pillow, Beige;” Amazon.com; (May 14, 2020); 18 pages; Retrieved May 25, 2022; retrieved from <URL: https://www.amazon.com/BulbHead-Inflatable-Elevates-Temporary-Swelling/dp/B07PDN3NRR.

Uprara; “ Mintiml Heaven Wedge;” uprara.com; (May 14, 2020); 5 pages; Retrieved May 25, 2022; retrieved from <URL: https://uprara.com/product/mintiml-heaven-wedge-5513492/?attribute_pa_title=default-title&gclid=EAIaIQobChMlibqkoYj89wIVLR-tBh2CygX3EAQYASABEgKSPfD_BwE>.

* cited by examiner

KYPHOTIC LIFT FOR MRI IMAGING BED

CROSS REFERENCE TO RELATED APPLICATIONS

This application claims priority to copending U.S. Provisional Patent Application Ser. No. 63/153,866, filed Feb. 25, 2021, and to copending U.S. Provisional Patent Application Ser. No. 63/179,898, filed Apr. 26, 2021, which are incorporated herein by reference in their entirety.

BACKGROUND

Kyphosis is a spinal disorder where an excessive outward curve of the spine results in an abnormal rounding of the upper back. The condition is sometimes known as "round-back," or in the case of a severe curve, as "hunchback." Kyphosis can occur at any age but is most common during adolescence and in the elderly. Prevalence and incidence of hyperkyphosis in older adults varies from approximately 20% to 40% among both men and women. Additionally, kyphosis can develop from either muscle weakness or degenerative diseases (e.g., osteoporosis). As the kyphosis angle increases, physical performance and quality of life often decline, making surgical intervention a priority. However, in the majority of cases, kyphosis causes few problems and does not require treatment. Occasionally, a patient may need to wear a back brace or perform exercises to improve his or her posture and strengthen the spine.

In severe cases, kyphosis can be painful, causing significant spinal deformity, thereby leading to breathing problems. Surgical intervention helps reduce the excessive curvature of the spine and is effective for eliminating pain. Currently, radiographic imaging is the gold standard for diagnosing the disorder as well as for treatment planning in those that require operation. Recently, magnetic resonance imaging (MRI) has been shown to be a useful adjunct for determining the disease stage and detecting the presence of abnormal structures on the spine that could cause neurological issues via pinching of nerves. Current methods to stabilize kyphotic patients during MRI imaging comprise manual lifts that lower the body onto the MRI table. The pelvis is raised using pillows and wedges to properly position the spine and head for imaging. It may take several tries with different sized pillows and wedges to get the pelvis supported at the appropriate height to perform the imaging. These approaches can subject the patient and clinical staff to unnecessary strain and injury. Also, improper positioning of the patient on the MRI bed can result in inaccurate imaging, subsequent additional imaging, burden to the patient, and out-of-pocket cost.

SUMMARY

A kyphotic lift can comprise a support base, and a body support secured to the support base at a first end. The body support can be movable away from the support base and can be operable to support at least an upper body of the patient during use. The kyphotic lift can also comprise a lift mechanism operable to raise and lower the body support segment away from and back towards the support base to position and align the patient's head with a magnetic resonance imaging (MRI) head coil.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 3C shows an approximate hinge position when the lift device is in its deflated condition. FIG. 3D shows the approximate hinge position when the lift is in its maximum raised operating condition. FIG. 3E shows the hinge position for disconnecting the hinge portions.

Figure 1A:
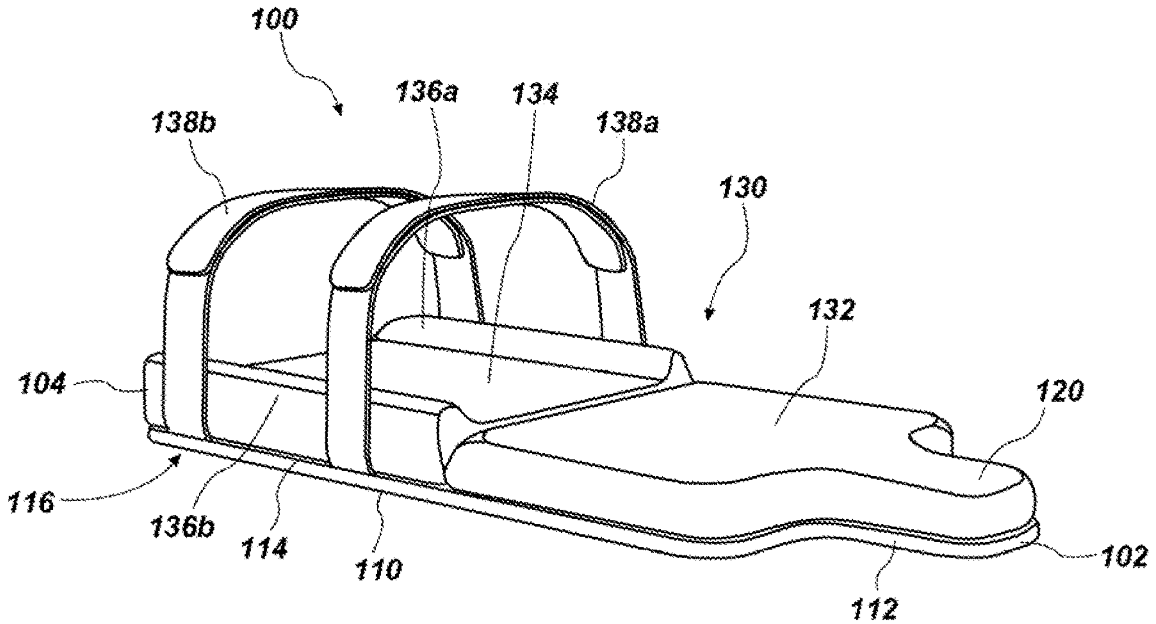
FIG. 1A is a schematic illustration of a patient lift device in a lowered state in accordance with one example.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a lift" includes reference to one or more of such mechanisms and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about"

generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "removably attached" means that the item can be attached and removed without the use of tools.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Patient Lift Device

The present disclosure describes a patient lift device that is placed on the gurney within the MRI scanner before a patient enters the machine such as for a diagnostic evaluation of kyphosis. The thoracic (rib cage) portion of the spine has a normal forward curvature in the range of 20 to 50 degrees as measured from T4 to T12. This forward curvature is matched by reverse curvatures called lordosis in the cervical spine (neck) and the lumbar spine (low back). Technically, any exaggerated rounding of the forward curvature in the upper back is called hyperkyphosis (too much kyphosis), but the term kyphosis is commonly used (and is used herein) to refer to the clinical condition of excess curvature of the upper back (T4 to T12) that is greater than 50 degrees that leads to a stooped forward posture. The kyphotic patient can be placed on top of the patient lift device, and the device can be raised, such as beneath the patient's pelvis, to stabilize and position the patient for imaging. The degree and distance that the device is raised can depend on the kyphosis angle and can be sufficient to orient a patient's head into the MRI head coil and to allow MRI imaging.

The patient lift device can be manufactured in various shapes and can accommodate several widely used and commercially available MRI platforms. The patient lift device can also accommodate different patient sizes (e.g. adolescent, adult, or obese individuals). This can be accomplished, for example, by a suitably wide body support, detachable auxiliary support surfaces, and/or straps.

The patient lift device can be accommodated on any MRI imaging platform and can allow for positioning before the patient has been placed within the MRI, although minor adjustments may also be made after the patient has been placed in the MRI. The patient lift position can be adjusted at a controlled speed to ensure the patient is positioned correctly before imaging. These features help reduce the risk of injury to the patient and medical provider as well as decrease the need for repeat imaging. The patient lift device can be constructed of MRI compatible materials that are also biocompatible with the skin. MRI compatible materials are materials that would not disturb the MRI's magnetic field. Such materials are generally non-ferromagnetic such as most plastics, aluminum, brass, titanium and so forth.

Figure 1B:
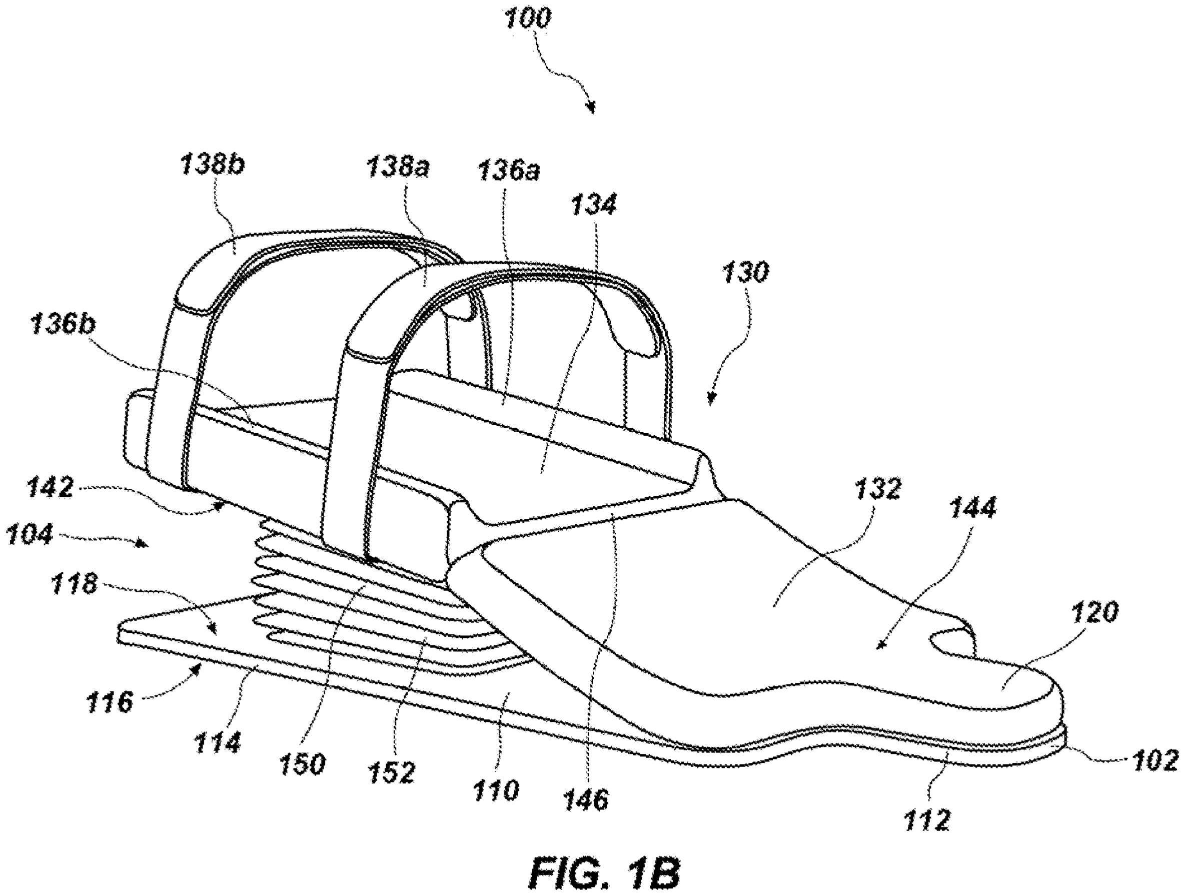
FIG. 1B is a schematic illustration of the patient lift device of FIG. 1A in a raised state.

An exemplary patient lift device is shown in FIGS. 1A-1B. FIGS. 1A and 1B show a schematic illustration of a kyphotic lift according to one example in the present disclosure. A kyphotic lift 100 can comprise a support base 110. The support base 110 can extend from a first end 102 to a second end 104 of the kyphotic lift 100 opposite to or distal from one another. Optionally, the kyphotic lift 100 can further comprise a shoulder support 120 and a body support 130. Thus, the kyphotic lift can also be provided without a shoulder support in any of the iterations described herein, such that shoulders directly contact an MRI bed.

The support base 110 can comprise a narrow portion 112 at the first end 102 of the kyphotic lift that corresponds to the shoulder support 120 and a wide portion 114 that corresponds to the body support 130. Accordingly, the support base 110 comprises an upper surface 118 that shares a common surface area with a lower surface 142 of the body support 130 when the kyphotic lift 100 is in a lowered position such as the position shown in FIG. 1A where the body support 130 is adjacent to the support base 110. The support base 110 can be a solid planar support base as shown in FIGS. 1A and 1B. In other examples, the support base 110 can comprise a friction enhancing device on a lower surface 116 thereof, such as a rubber strip adhered to the lower surface 116. Other friction enhancing materials can also be used such as, but not limited to, textured surfaces, rubberized surfaces, tacky surfaces, and the like. The support base 110 can also comprise one or more flanges or other features that can be used to position the support base 110 on an MRI bed, or that can be utilized to orient and position the body support 130 relative to the support base 110.

The shoulder support 120 can be secured to the support base 110 in such a manner to prevent relative movement between the shoulder support 120 and the support base 110 during use. As shown in FIGS. 1A and 1B, the shoulder support 120 can be secured to the support base 110 to the narrow portion 112 of the support base 110 at the first end 102. In this example, the shoulder support 120 can be flexibly connected to the body support 130. The body support 130 can be configured to be raised and lowered relative to the support base 110. The body support 130 can comprise a torso support segment 132 and a hip support segment 134. The torso support segment 132 can be flexibly connected to the shoulder support 120 at a hinge 144 or directly to the support base 110. The hinge 144 can be a "living hinge" (i.e. a thin, flexible hinge oftentimes made from the same material as the two pieces it connects). Similarly, the hip support segment 134 can be flexibly connected to the torso support segment 132 at a hinge 146, which can also be a living hinge. Thus, in this example, the shoulder support 120 and the body support 130 can be formed as a single, unitary part. In other examples, the shoulder support 120 and the body support 130 can be formed separately and can be flexibly connected by a hinge, such a living hinge or other low profile hinge. Similarly, the torso support segment 132 and the hip support segment 134 can be formed separately and can be flexibly connected via a living hinge or other low profile hinge. While the torso support segment 132 and the hip support segment 134 are shown to be hinged together, they may also comprise a unitary non-hinged support piece.

An upper surface of the body support 130 can comprise a foam pad for patient comfort. The foam pad can also be contoured to provide improved retention of a patient and additional comfort to the patient. The foam pad can be optionally removably attached to the upper surface to facilitate cleaning, repair, or replacement. Further, the supper surface can include a friction enhancing mechanism or surface to reduce patient movement during use. Non-limiting examples of suitable friction enhancing surfaces can include a rubber strip, textured surfaces, rubberized surfaces, tacky surfaces, and the like.

The body support 130 can further comprise safety straps 138. In this example, a first safety strap 138*a* and a second safety strap 138*b* can be attached to the hip support segment 134 that can help to secure a patient to the kyphotic lift 100. However, the safety straps 138*a*, 138*b* can be incorporated on the torso support segment 132 and/or the shoulder support 120 as needed. The safety straps 138*a*, 138*b* can comprise straps extending from sides of the body support 130 that can be selectively connected and disconnected via a clip, a hook-and-loop fastener, or the like. Each strap can either be a continuous strap extending under the body support 130 or comprise separate straps extending from each side of the body support 130. In either case, the strap can be removably attached to the body support 130 to facilitate ease of cleaning. The body support 130 can further comprise raised side edges 136*a*, 136*b* that can further aid in the positioning of the patient on the body support 130. These raised side edges 136*a*, 136*b* can be integrally formed as part of the body support 130, such as part of the hip support segment 134, or can be separate pieces which are attached along edges of the body support 130. The raised edges can generally have a height of 0.5 to 3 inches.

The kyphotic lift 100 further comprises a lift mechanism 150. The lift mechanism 100 can be operable to raise the body support 130 away from the support base 110. The lift mechanism 150 can be pneumatic, hydraulic, mechanical, or other mechanism which allows for the body support 130 to be raised and lowered with respect to the support base 110 and the MRI bed. In one alternative, the kyphotic lift 100 can omit the support base 110 and can utilize an MRI bed directly as a support base. In such cases, the shoulder support 120 and/or body support can optionally include a friction enhancing surface such as those previously described, and/or other mechanism to secure the kyphotic lift 100 to the underlying MRI bed to increase stability. In cases where the support base 110 is not used, the kyphotic lift 100 and upper body support may be affixed to the MRI bed with straps, hook and loop fasteners or other fastening means known to those of skill in the art.

In one option, the lift mechanism 150 can comprise a collapsible housing 152. For example, the collapsible housing 152 can comprise accordion folding walls as shown in FIG. 1B. Such a housing can reduce chances of inadvertent pinching of the patient or technicians during raising or lowering of the kyphotic lift 100 if a mechanical lift is used. However, such a collapsible housing 152 may also be pneumatically inflated with one or more internal inflatable chambers. Both the housing and the lift mechanism of the kyphotic lift 100 may be accommodated in a pocket in the hip support segment 134 and/or the torso support segment 132 allowing the hip support segment 134 and the torso support segment 132 to be supported directly on the support base in the lowered position. This provides stability when loading the patient onto the kyphotic lift 100.

The lift mechanism 150 can be operated in a lowered state, such as shown in FIG. 1A, in which the body support 130 is substantially coplanar with the shoulder support 120, and can be maneuvered to a raised state in which the body support 130 is raised away from the support base 110, as shown in FIG. 1B. The lift mechanism 150 can further be operated to raise the body support 130 to any position higher or lower than that shown in FIG. 1B to accommodate the needs of a specific patient. In one option, when the lift mechanism 150 is in a raised state, the body support 130 is raised away from the support base 110, and the shoulder support 120 remains fixed to the support base 110 as shown in FIG. 1B. For example, the lift mechanism 150 can lift the hip support segment 134 and the torso support segment 132 away from the support base 110.

The lift mechanism 150 can be attached to the hip support segment 134 and can raise the hip support segment 134 and the torso support segment 132 via the hinge 146 between the hip support segment 134 and the torso support segment 132. In another example, the lift mechanism can alternatively be attached to both the hip support segment 134 and the torso support segment 132.

Figure 2:
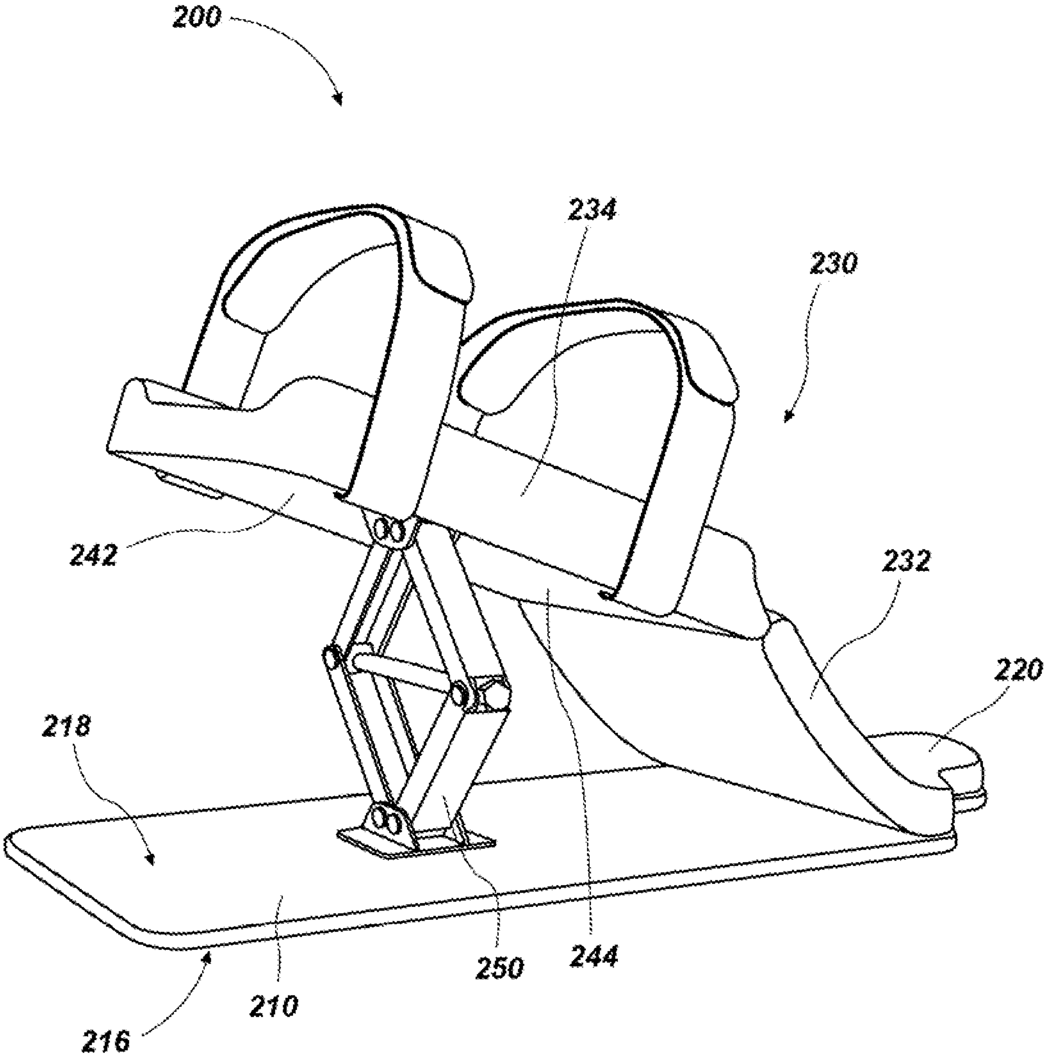
FIG. 2 is a schematic illustration of a patient lift device in a raised state using a mechanical scissor lift in accordance with one example.

Another example of a patient lift device in shown in FIG. 2. In this example, a kyphotic lift 200 is similar to the kyphotic lift 100 in that it comprises a support base 210, a shoulder support 220 and a body support 230 comprising a torso support segment 232 and a hip support segment 234. In one option, the kyphotic lift 200 comprises a hollowed-out portion 244 on the lower surface 242 of the body support 230. The hollowed-out portion 244 can be configured to accommodate the lift mechanism 250 when the lift mechanism 250 is in the lowered state and the lower surface 242 of the body support 230 moves adjacent with the upper surface 218 of the support base 210. A lower surface 216 of the support base 210 can optionally include a friction enhancing material as previously described.

The lift mechanism 250 in this example can comprise a scissor assembly having a lowered state in which the body support 230 and the shoulder support 220 are substantially planar, and a raised state in which the body support 230 is raised away from the support base 210. The scissor assembly can be disposed within the hollowed-out portion of the hip support segment when in the lowered state. In this case, the lift mechanism 250 can be formed of a non-ferromagnetic material. Non-limiting examples of suitable non-ferromagnetic materials can include Ti, Co—Cr alloys, copper, non-ferromagnetic stainless steels, ceramics, polymers, carbon fibers, Kevlar, glass filled nylon, fiber reinforced polymers, and the like. Further, specialized non-ferrous metal alloys, urethanes, silicones, slip-resistant coating for bottom of base etc. can also be used.

Figure 3A:
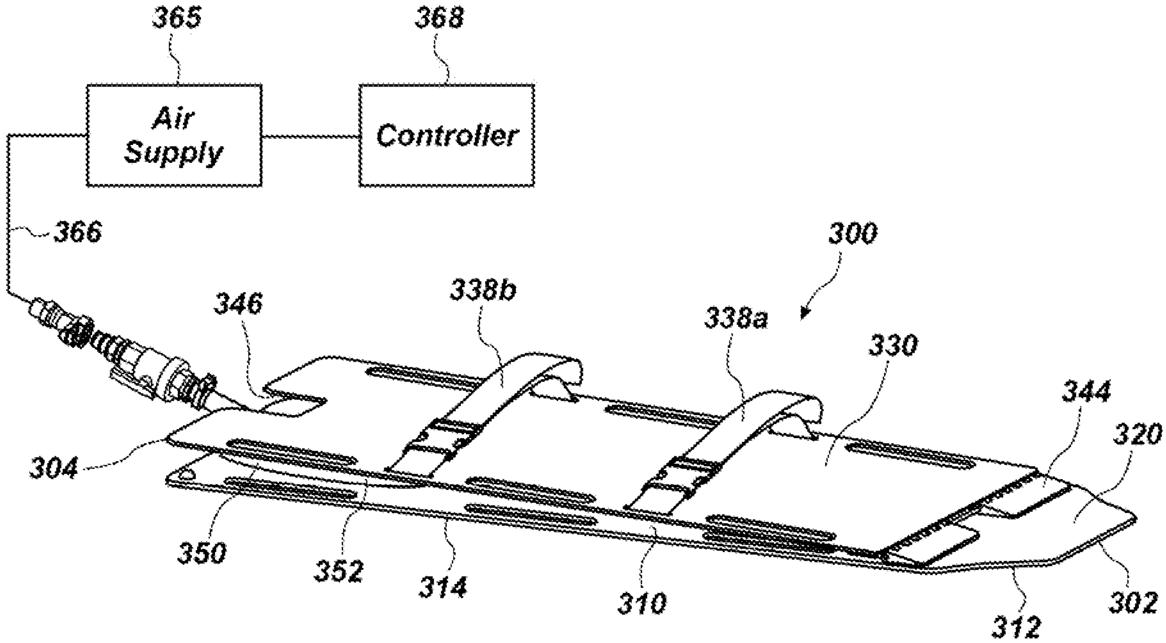
FIG. 3A is a schematic illustration of a patient lift device in a lowered state in according with one example.
Figure 3B:
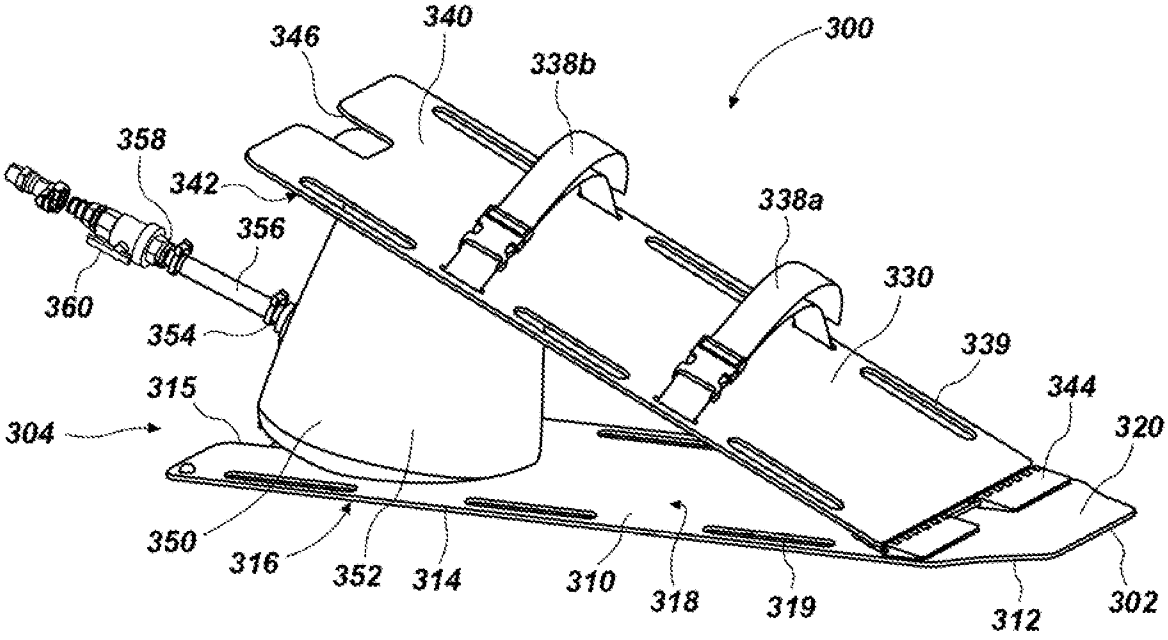
FIG. 3B is a schematic illustration of the patient lift device of FIG. 3A in a raised state.

FIG. 3A is a schematic illustration of a patient lift device in a lowered state in according with one example, and FIG. 3B is a schematic illustration of the patient lift device of FIG. 3A in a raised state. In this embodiment, to facilitate the patient being able to get on and off of the kyphotic lift 300, the overall height of the lift can be kept to a minimum. In FIGS. 3A and 3B, a patient lift device can be a kyphotic lift 300 that comprises a support base 310, a body support 330, and lift mechanism 350 operable to lift the body support 330 away from the support base 310 to raise the hips of a patient on the kyphotic lift 300.

The support base 310 can comprise an optional shoulder support 312 disposed on a first end 302 of the kyphotic lift 300. The shoulder support 320 can be on a narrow portion of the support base 310 at the first end 302. In other words, in this example, the shoulder support 320 and the support base 310 can be formed integrally. The support base 310 can further comprise a wide portion 314 that corresponds with the body support 330 of the kyphotic lift 300. The body support 330 can also include a lower surface 316 and an upper surface 318.

In this example, the body portion 330 can be a single, rigid member that is hingedly connected to the support base 310 via a low-profile hinge 344. The low-profile hinge 344 can connect to the support base 310 near the first end 302 and generally between the shoulder support 312 and the wide portion 314 of the support base 310. The body portion 330 and the support base 310 may be comprised of a fiberglass or carbon fiber reinforced polymer to provide rigidity and the required strength when raising a patient, yet be thin so as to maintain the low profile of the kyphotic lift 300. The thickness of the body portion 330 and support base 310 may vary between ¼ inch and 1.0 inch, such as ½ inch.

Figure 3C:
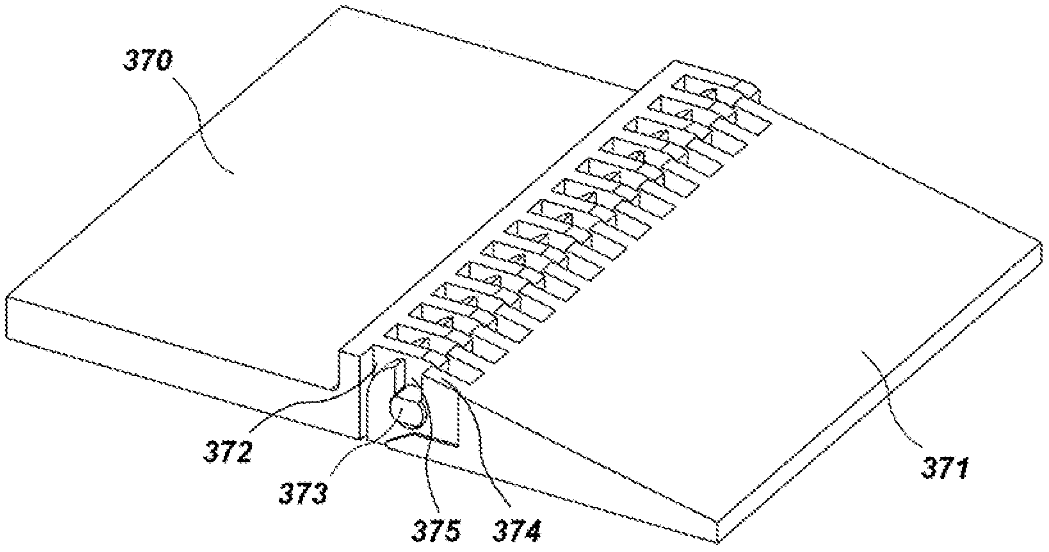
FIGS. 3C, 3D and 3E are schematic sectional views through a center of a low profile hinge (344).
Figure 3D:
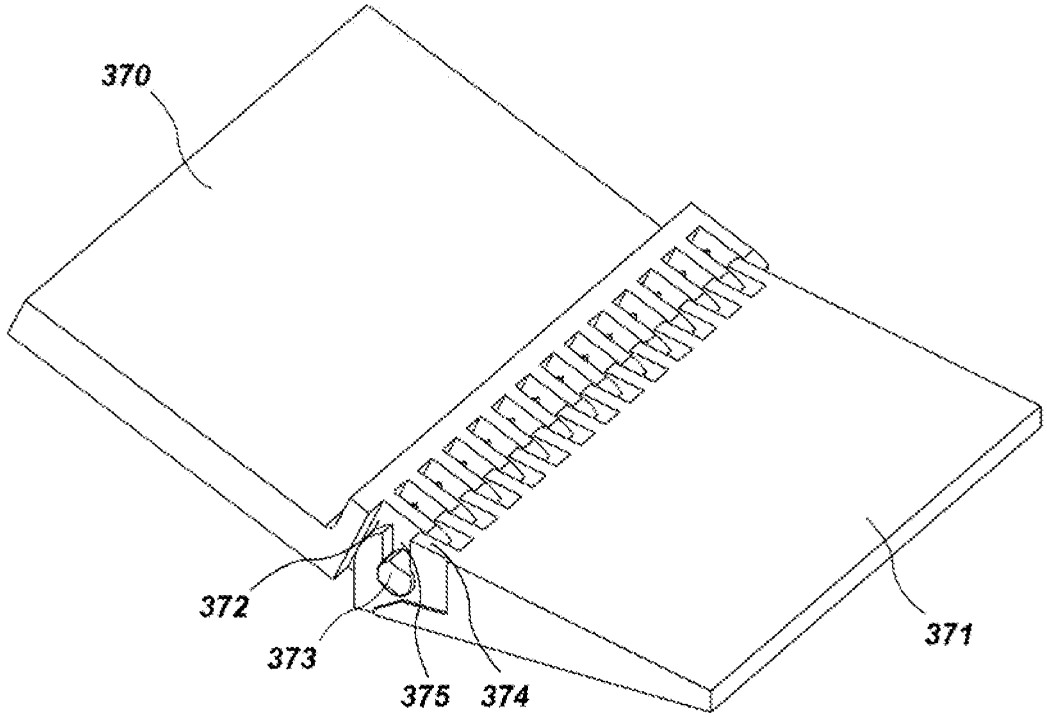
Figure 3E:
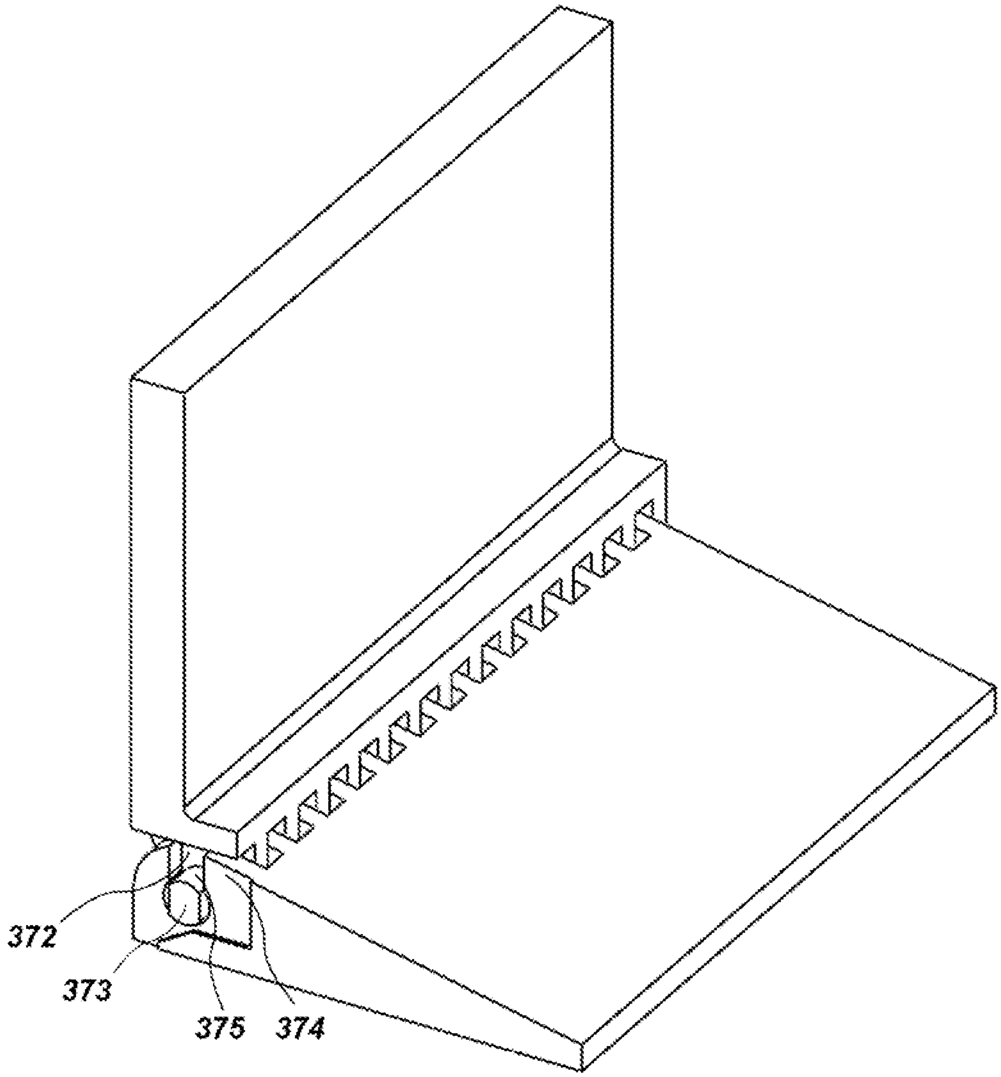

The low profile hinge 344 is further shown in section views 3C, 3D and 3E. The low profile hinge 344 comprises two portions, the body connection portion 370 and the base connection portion 371. Body connection portion 370 is configured with an "L" shape to accommodate the thickness of the body portion 330. These portions can be connected using an adhesive, adhesive tape or other fasteners known to one of skill in the art. Likewise, the base connection portion 371 can be connected to the support base 310 using an adhesive, adhesive tape or other fasteners known to one of skill in the art. The base connection portion 371 can be wedge shaped so as to be more comfortable for the patient lying on the lift. The body connection portion 370 can comprise a plurality of fingers 372 with at least one integral hinge pin 373 therebetween. Hinge pin 373 can have flats on opposing sides. Base connection portion 371 can comprises at least one finger 374. Finger 374 comprises a slot 375 whose width corresponds to the distance between the flats on the hinge pin 373 with a cylindrical area at the bottom of the slot that corresponds to the hinge pin 373 diameter. As best shown in FIG. 3C, when the hinge is in the flat position corresponding to the collapsed condition of the kyphotic lift 300, the hinge pin 373 is rotated in the cylindrical area such that the diameter of the pin is larger than the slot 375, thus the two hinge portions 370 and 371 are rotationally locked together. As best shown in FIG. 3D, as the body portion 330 is rotated upward and its attached body connection portion 370 of the hinge rotates up, it ends in the approximate position shown in FIG. 3D. In this hinge position, the first hinge portion 370 has rotated up from the flat at least 10 degrees, in some cases at least 20 degrees and in yet other cases at least 25 to 30 degrees. This angle can be significantly larger but actual use has found that these upper angles are adequate to position the head and neck for the vast majority of kyphotic patients. In this position, although the hinge pin 373 is rotated in the cylindrical area somewhat from the flat position, the diameter of the pin is still larger than the slot 375 and the two hinge portions 370 and 371 are still rotationally locked together. As best shown in FIG. 3E, when it is desired to disassemble the kyphotic lift 300 for cleaning or other purposes, the inflatable cushion 352 can be removed as discussed below and the body portion 330 then rotated vertically. In this position, the flats on hinge pin 373 are now vertical and align with the slot 375. The hinge can now be pulled apart by pulling the body portion 330 upward, while the hinge cannot be separated when in other rotational positions. Multiple or thicker fingers can be used to increase the strength of the hinge. A person of skill in the art would understand that the hinge portion with the pin can also be on the base connection portion 371 and the hinge portion 371 with the slot could on the body connection portion 370.

The lift mechanism 350 can comprise an inflatable assembly having an inflatable cushion 352 that can selectively inflate and deflate to move the body support 330 away from the support base 310 to raise and lower a patient's hips on the kyphotic lift 300 by engaging with a lower surface 342 of the body support 330. The inflatable cushion 352 is releasably connected to the support base 310 with a material flap (not shown) that may be ultrasonically welded to the bottom inflatable cushion 352. In turn, the material flap may be inserted into a hole in the support base 310 and releasably affixed to the lower surface 316 by a suitable mechanism, e.g. hook and loop fasteners. Alternatively, the inflatable cushion or the material flap may be releasably affixed to the upper surface 318. Likewise, the cushion 352 may have a material flap (not shown) that may be ultrasonically welded the top. This material flap or the top of the inflatable cushion 352 may releasably affixed to the body support 330 by a suitable mechanism, e.g. hook and loop fasteners. In this manner the inflatable cushion 352 can be removed in the event it needs to be replaced or for cleaning purposes.

In this example, the inflatable cushion 352 can comprise an inlet/outlet 354 to which a flexible hose 356 can be attached. The inlet/outlet can be a single connection opening or a connection opening for the inlet and a separate connection opening for the outlet. In this example, the body support 330 can comprise a cutout 346 and the support base 310 can comprise a corresponding cutout 315 that are disposed on the second end 304 of the kyphotic lift. The cutouts 346, 315 can accommodate the inlet/outlet 354 and flexible hose 356 such that the inlet/outlet 354 and flexible hose 356 do not interfere with the body support 330 or support base 310 when the inflatable cushion 352 is in the deflated state, such as shown in FIG. 3A. In this manner the kyphotic lift 300 can be collapsed to a substantially flatter condition in the deflated state as the inlet/outlet 354 and flexible hose 356 are not between the support base 310 and the body support 330. Additionally, the inflatable cushion 352 can be shaped as an oblique truncated cone. The kyphotic lift 300 can lift to an angle of at least 10 degrees, but in some cases to 20 degrees and in many cases to 25 to 30 degrees so as to accommodate the kyphotic patient. The angle between the top and bottom surface of the oblique truncated cone matches the maximum lift angle. The top circular surface of the inflatable cushion 352 can be positioned offset from the bottom circular surface such that when the body support 330 rotates down toward the support base about hinge 344 the circular surfaces are approximately concentric. In this example, the top circular surface is smaller than the bottom circular surface, and the sidewalls of the inflatable cushion 352 collapse accordion-like and progressing outward from the smaller top surface as the body support 330 descends toward the support base 310. In this fashion the collapsed inflatable cushion 352 takes up a relatively smaller amount of space between the body support 330 and the support base 310 for a more compact kyphotic lift 300 in the collapsed condition. As discussed, keeping the height of the kyphotic lift 300 low in the deflated state and compact eases being able to position the patient on the kyphotic lift 300.

The flexible tube 356 can connect to a valve assembly 358 comprising a valve that can be selectively turned on and off via a handle 360 to control air flow to the inflatable cushion 352. The valve assembly 358 can be connected to an air supply 365 via a conduit 366. In some examples, the air supply is a hand pump or foot pump. A foot pump can allow the operator to be in an upright position and have the use of their hands to assist the patient as needed. The angle to which the body support 330 is elevated away from the support base 310 can be precisely controlled such that the position of the patient's spine and head are positioned properly for imaging. Once the patient is positioned properly, the valve assembly 358 can be shut off and the pump can be disconnected using a quick disconnect that is between the pump hose and the valve assembly 358. Even with the pump disconnected the patient will stay in the proper position. When the imaging is complete, the valve handle 360 can be turned such that air is released from the inflatable cushion 352 in a controlled manner to let the patient down essentially flat with the MRI table.

In some examples, the air supply 365 can be an air compressor or similar device to provide pressurized air to the inflatable cushion 352 to cause the lift mechanism 350 to raise the body support 330 away from the support base 310, as shown in FIG. 3B. The air supply 365 can further comprise a release valve (not shown) to release pressure from the inflatable cushion 352 to lower the body support 330 towards the support base 310. With the inflatable assembly as the lift mechanism 350, the inflation can be controlled via the air supply 365, which allows the technician or medical provider to incrementally adjust inflation to precisely position the patient's pelvis for imaging the spine and head. Additionally, inflation removes the requirement of the medical staff to manually move the patient, thereby avoiding risk of injury to either individual.

In some examples, the air supply can be connected to a controller 368 as shown in FIG. 3A. The controller 368 can be operable to actuate the air supply 365 to add or remove air from the inflatable cushion 352 to raise and lower the body support 330 relative to the support base 310. The controller 368 can be any suitable control device and can comprise one or more inputs operable by a technician or other medical professional to control the air supply 365. The controller 368 can also be an automated or semi-automated device comprising control instructions stored in a memory. The controller 368 can execute the control instructions to control the operation of the air supply 365 based on one or more inputs from a technician, a sensor connected to the controller or the kyphotic lift 300, and the like. The overall inflatable assembly can be designed to control the inflation of the inflatable cushion 352 to accommodate a variety of small incremental changes in positioning required for MRI imaging. When using a controller, control instructions can be input directly by a technician (i.e. raise or lower). However, in some alternatives, one or more sensors can be used to determine a height of the body support relative to the base or MRI bed, inflation pressure, and the like. These sensors can then provide feedback to the controller to determine when additional inflation or deflation is desired to obtain a target height.

In some examples, the kyphotic lift 300 can be configured to be portable. For example, the kyphotic lift 300 can be configured and operable to be easily move onto or off of an MRI bed. The support base 310 can thus comprise one or more handles 319 formed as elongated holes through the support base 310. Similarly, the body support 330 can comprise one or more handles 339 formed as elongated holes through the body support 330. The handles 339 can be configured to align with the handles 319 when the body support is in the lowered position as shown in FIG. 3A. This can allow the technician to easily transport the kyphotic lift 300 as needed.

Similar to kyphotic lifts 100, 200, the kyphotic lift 300 can comprise safety straps 338*a*, 338*b* disposed on the body support 130. The safety straps 338*a*, 338*b* can help secure the patient to the kyphotic lift 300 during use. As one example, safety straps 338*a*, 338*b* can be oriented in a forward (hip region) and rearward position (mid-thigh region) along the body support 330, respectively. Such restraints can reduce chances of the patient sliding off of the lift during use. The safety straps kyphotic lift 300 can be held in position axially by slots in the body support 330. Each strap can extend completely under the body support 330 or extend as separate straps, one from each side slot. Such safety straps can be removably connected to the underside 342 by a suitable mechanism such as, but not limited to, hook and loop fasteners, snaps, buttons, and the like.

Figure 4A:
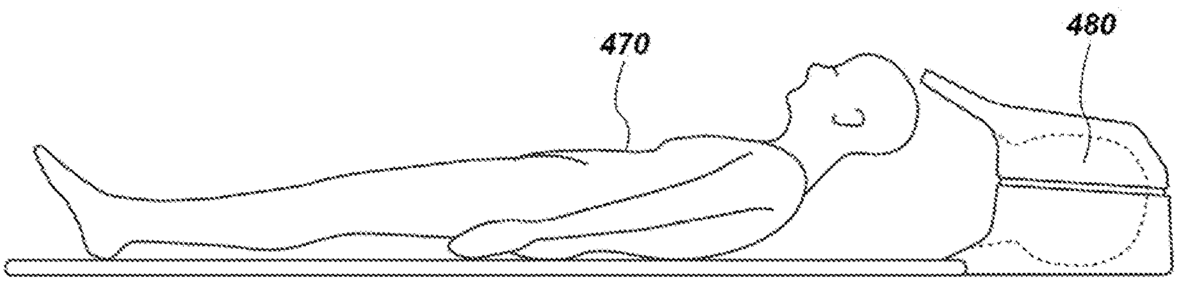
FIG. 4A is a schematic illustration of a kyphotic patient without a patient lift device and FIG. 4B is a schematic illustration of the kyphotic patient with the patient lift device in accordance with one example.
Figure 4B:
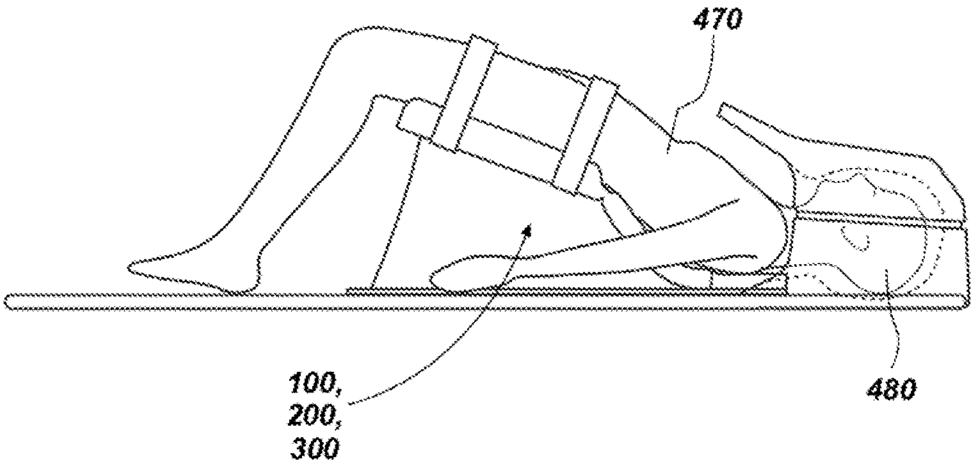

Kyphotic lift 300 can also have a removable cushion (not shown) which is removably connected to the top surface of the body support 330. This cushion can be made to be disposable for sanitary purposes. The cushion can also provide a high friction surface that resists the tendency of the patient to slide down the raised portion of the kyphotic lift 300. FIG. 4A is a schematic illustration of a kyphotic patient 470 without a patient lift device and FIG. 4B is a schematic illustration of the kyphotic patient 470 with the patient lift device in accordance with one example. The kyphotic lift devices 100, 200, 300 discussed herein can help position a patient suffering from kyphosis such that the patient's head can comfortably fit within a head coil 480 for an MRI. As shown in FIG. 4A, a patient suffering from kyphosis cannot easily fit into a head coil 480 of an MRI device if laying on a flat surface. The head coil 480 is generally not positionable. As shown in FIG. 4B, using the kyphotic lift 100, 200, 300, the patient's hips can be raised such that the patient's head can align with and fit comfortably within the MRI head coil 480.

As an example, referring to FIGS. 1A-4B, the patient can be placed on top of a kyphotic lift 100, 200, 300. The kyphotic lift 100, 200, 300 can be raised by lifting the body support 130, 230, 330 away from a support base 110, 210, 310. The kyphotic lift 100, 200, 300 can be raised by a lifting mechanism, such as via an inflatable assembly, a scissor lift, or the like. When using the lifting mechanism, the height can be incrementally adjusted by the technician or other medical provider to precisely position the pelvis of a patient for imaging, and to allow a patient's head to align with and be received in a standard MRI head coil as illustrated generally in FIG. 4B. In the raised state, the body support 130, 230, 330 can have an inclined surface that supports the patient's torso, pelvis, and upper leg portion. The kyphotic lift 100, 200, 300 can also have straps to secure the patient.

The patient lift device may be used for patients with kyphosis, lordosis, scoliosis, or the like. Alternatively, the patient lift device can be used for physical therapy.

In another example, the lift mechanism can be an inflatable assembly including a plurality of independently inflatable cushions. Referring to any of FIGS. 1A through 4B, the lift mechanisms illustrated can be replaced with an inflatable assembly. For example, for a segmented body support as in FIG. 1A through 2, the plurality of independently inflatable cushions can include at least one hip support cushion disposed below a hip support segment, and at least one torso support cushion disposed below a torso support segment. In this manner, each cushion can be inflated to provide custom elevation for each segment based on a patient position and comfort.

Figure 5:
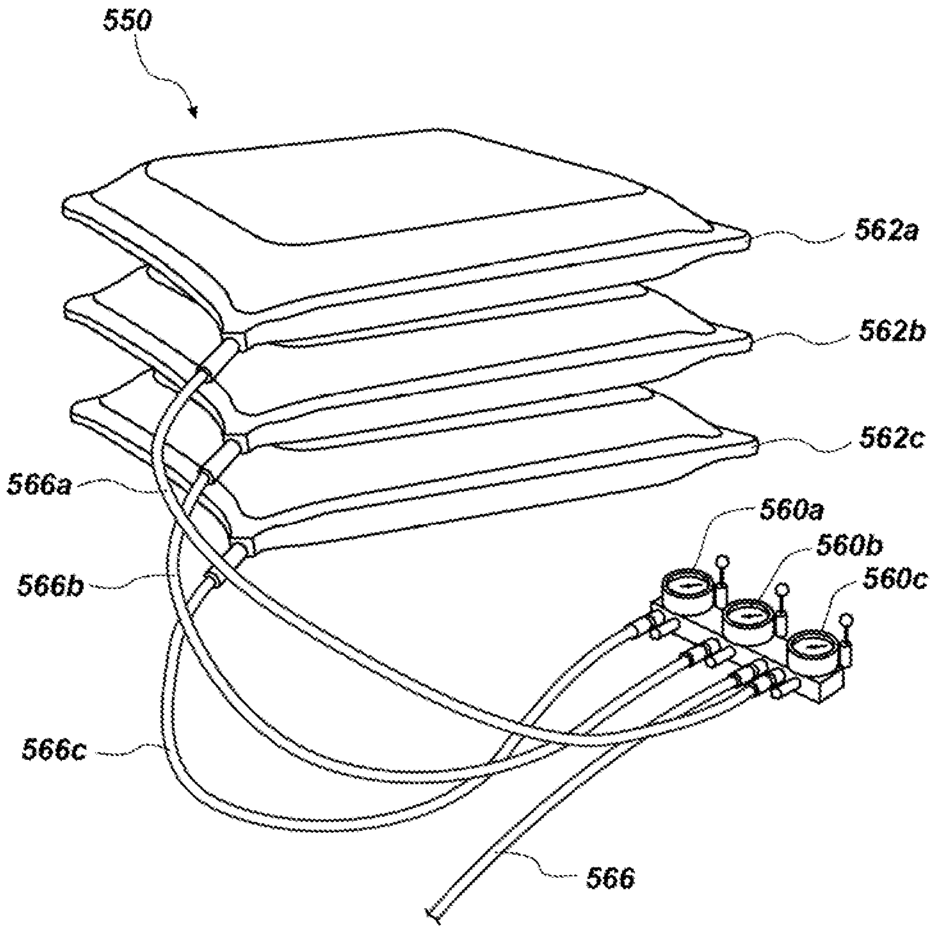
FIG. 5 is a schematic illustration of an inflatable lift mechanism having a set of three independently inflatable cushions in another example.

FIG. 5 is a schematic illustration of an inflatable lift mechanism having a set of three independently inflatable cushions in another example. While three cushions are shown in this example, more or less inflatable cushions can be used. Further, while the inflatable cushions in this example are shown stacked on top of one another, inflatable cushions could also be arranged adjacent to one another. Further, such inflatable lift mechanisms can be used in any of the kyphotic lifts described herein (e.g. FIGS. 1A-4B). In this example, the inflatable assembly 550 can optionally include a plurality of independently inflatable cushions 562*a*, 562*b*, 562*c*.

In this configuration, the pressure in each of the air cushions 562*a*, 562*b*, 562*c* can be controlled individually, that is each air cushion 562*a*, 562*b*, 562*c* can maintain a different internal pressure than other air cushions 562*a*, 562*b*, 562*c*. Alternatively, the internal pressure in each air cushion 562*a*, 562*b*, 562*c* can be the same as in other air cushions 562*a*, 562*b*, 562*c*. A user can selectively control the internal pressure in the air cushions 562*a*, 562*b*, 562*c* to achieve a desired height of the inflatable lift. The air cushions 562*a*, 562*b*, 562*c* can be connected to flexible hoses 556*a*, 556*b*, 556*c*, respectively. Each flexible hose 556*a*, 556*b*, 556*c* can be connected to an air supply conduit 566 by way of a valve assembly including corresponding valves 560*a*, 560*b*, 560*c*. The valves 560*a*, 560*b*, 560*c* can be operable to control the air pressure in each individual air cushion 562*a*, 562*b*, 562*c*, respectively.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A kyphotic lift, comprising:

a support base, wherein the support base is a planar substrate that is adapted to be positioned onto an existing MRI bed;

a body support including a first end secured to the support base and a second end opposite the first end, the body support including a torso support segment and a hip support segment, the body support being movable away from the support base and being operable to support at least a chest and an abdomen of a patient during use; and a lift mechanism operable to raise and lower the second end of the body support away from and towards the support base to a position where the hip support segment is above the torso support segment such that hips and thighs of the patient are above the torso and to position and align a head of the patient with a magnetic resonance imaging (MRI) head coil.

2. The lift of claim 1, further comprising a shoulder support operable to support shoulders of a patient during use and wherein the shoulder support is formed integrally with the support base.

3. The lift of claim 1, wherein the support base comprises an upper surface that shares a common surface area with a lower surface of the body support, and wherein when the lift mechanism lowers the body support towards the support base, the body support is lowered to be adjacent to the support base, the support base being a solid planar support base.

4. The lift of claim 1, wherein the support base and the body support are flexibly connected to one another.

5. The lift of claim 1, wherein the support base is rigid, the body support is planar and rigid, and the support base is rotationally connected to the first end of the body support via a hinge.

6. The lift of claim 1, wherein the body support comprises a torso support segment and a hip support segment, and wherein the torso support segment is flexibly connected to the hip support segment.

7. The lift of claim 1, wherein the body support further comprises raised side edges.

8. The lift of claim 1, wherein the lift mechanism is an inflatable assembly having an inlet and outlet; the inflatable assembly having a deflated state in which the second end of the body support is adjacent to the support base, and an inflated state in which the second end of the body support is raised away from the support base, wherein the inlet and outlet are either a common opening or two separate openings.

9. The lift of claim 8, wherein the inflatable assembly includes a plurality of independently inflatable cushions.

10. The lift of claim 9, wherein the body support comprises a torso support segment and a hip support segment, wherein the torso support segment is flexibly connected to the hip support segment, and wherein the plurality of independently inflatable cushions comprises at least one hip support cushion disposed below the hip support segment and at least one torso support cushion disposed below the torso support segment.

11. The lift of claim 9, wherein two or more of the plurality of independently inflatable cushions are stacked on top of one another.

12. The lift of claim 9, wherein the inflatable assembly is removably attached to the body support and/or the support base.

13. The lift of claim 9, comprising a cutout in the second end of the body support and/or the support base such that the inlet and/or outlet is not between the body support and the support base in the deflated state of the inflatable assembly.

14. The lift of claim 9, comprising an air supply and control system for controlling the amount of air into the inflatable assembly, and wherein the air supply and control system is a hand pump or foot pump that is removably attached to the inflatable assembly.

15. The lift of claim 8, wherein the inflatable assembly comprises a collapsible housing.

16. The lift of claim 8, wherein the body support comprises a hollowed-out portion on a lower side thereof, and wherein the inflatable assembly is disposed within the hollowed-out portion of the body support in the deflated state.

17. The lift of claim 8, wherein the inflatable assembly is a truncated cone.

18. The lift of claim 17, wherein the inflatable assembly is an oblique truncated cone, wherein a top of the oblique truncated cone and a bottom of the oblique truncated cone are substantially concentric in the deflated state.

19. The lift of claim 1, wherein the lift mechanism comprises a scissor assembly having a lowered state in which the body support is adjacent to the support base, and a raised state in which the body support is raised away from the support base.

20. The lift of claim 19, wherein the body support comprises a hollowed-out portion on a lower side thereof, and wherein the scissor assembly is disposed within the hollowed-out portion of the body support in the lowered state.

21. The lift of claim 1, further comprising patient belt straps oriented to secure a patient to the body support.

22. The lift of claim 1, comprising at least one hole adjacent the edge of body support or support base for gripping the kyphotic lift for positioning on the MRI machine or for transport of the kyphotic lift.

23. The lift of claim 1, wherein the lift mechanism is configured to contact and provide lifting force against only a subsection of the body support.

24. The lift of claim 23, wherein the subsection is disposed closer to the second end of the body support than the first end of the body support.

25. A method of supporting a patient with kyphosis during magnetic resonance imaging (MRI), the method comprising:

placing a patient on a body support of a kyphotic lift having a lift mechanism, wherein the body support is operable to support an upper body of the patient including at least a chest and an abdomen of the patient;

lifting the body support away from an MRI bed with the lift mechanism to raise hips of the patient to a position where the hips and thighs of the patient are above the torso;

positioning a head of the patient to align with an MRI head coil;

performing MRI imaging using the MRI head coil to produce a patient image; and lowering the body support toward the MRI bed with the kyphotic lift to lower the hips of the patient toward the MRI bed.

26. The method of claim 25, wherein air is pumped into an inflatable assembly as part of the lift mechanism lifting the body support away from an MRI bed and air is released from the inflatable assembly for lowering the body support toward the MRI bed.

27. A kyphotic lift, comprising:

a rigid support base, wherein the support base is a planar substrate that is adapted to be positioned onto an existing MRI bed;

a planar, rigid body support including a first end rotationally secured, via a hinge, to the support base and a second end that is free to lift relative to the support base, the body support including a torso support segment and a hip support segment, the body support being movable away from the support base by rotating at the hinge and being operable to raise at least a chest and an abdomen of the a kyphotic patient during use; and a lift mechanism disposed between the support base and the body support and configured for lifting the second end of the body support relative to the support base, via rotation at the hinge, to a position where the hip support segment is above the torso support segment such that hips and thighs of the kyphotic patient are above the torso and such that the head of the kyphotic patient is positionable in an MRI head coil.

28. The lift of claim 27, wherein the lift mechanism is configured to contact and provide lifting force against only a subsection of the body support.

29. The lift of claim 28, wherein the subsection is disposed closer to the second end of the body support than the first end of the body support.

* * * * *